United States Patent [19]

VandenBerg

[11] Patent Number: Plant 7,515

[45] Date of Patent: May 7, 1991

[54] CHRYSANTHEMUM PLANT NAMED OCASO

[75] Inventor: Cornelis P. VandenBerg, Salinas, Calif.

[73] Assignee: Yoder Brothers, Inc., Barberton, Ohio

[21] Appl. No.: 469,821

[22] Filed: Jan. 24, 1990

[51] Int. Cl.[5] ..... A01H 5/00

[52] U.S. Cl. ..... Plt./74

[58] Field of Search ..... Plt./74

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Chrysanthemum plant named Ocaso particularly characterized by its flat capitulum form; daisy capitulum type; orange-bronze ray floret color; diameter across face of capitulum of 83 to 89 mm when fully opened; photoperiodic flowering response to short days of 45 to 49 days when grown in Salinas, Calif., and 62 to 65 days when grown in Bogota, Colombia; peduncle length of the first lateral of 15 to 20 cm, and of the fourth lateral of 18 to 23 cm, when grown without growth regulator applications, on open, terminal sprays; plant height of 86 to 102 cm when grown as a single stem spray cut mum in Salinas, Calif. with 6 to 8 long days prior to start of short days; height of 94 to 112 cm when grown in Bogota, Columbia with 14 to 15 long days prior to start of short days; and excellent tolerance to low night temperatures for bud initiation and flower development.

3 Drawing Sheets

1

The present invention comprises a new and distinct cultivar of Chrysanthemum, botanically known as *Dendranthema grandiflora,* and referred to by the cultivar name Ocaso.

Ocaso, identified as 84-218015, was originated from a cross made by Cornelis P. VandenBerg in a controlled breeding program in Salinas, Calif., in 1983.

The female parent of Ocaso was an unnamed seedling, identified as 79-914017, and described as a pink-purple daisy spray cut mum. The male parent of Ocaso was an unnamed seedling, identified as 77-358001, and described as an orange-bronze daisy spray cut mum.

Ocaso was discovered and selected as one flowering plant within the progeny of the stated cross by Cornelis P. VandenBerg in December 1984, in a controlled environment in Salinas, Calif.

The first act of asexual reproduction of Ocaso was accomplished when vegetative cuttings were taken from the initial selection in February 1985 in a controlled environment in Salinas, Calif., by technicians working under the supervision of Cornelis P. VandenBerg.

Horticultural examination of controlled flowerings of successive plantings has shown that the unique combination of characteristics as herein disclosed for Ocaso are firmly fixed and are retained through successive generations of asexual reproduction.

Ocaso has not been observed under all possible environmental conditions. The phenotype may vary significantly with variations in environment such as temperature, light intensity and daylength. For example, plant height will increase with an increased number of long days after planting prior to start of short days. Under low night temperatures (10 degrees Celsius and lower) flowering can be expected to be delayed. Under high temperatures (25 degrees Celsius night and 35 degrees Celsius day) flowering can be expected to be delayed and be more uneven than under normal temperatures. Normal temperatures can be described as 15 degrees Celsius minimum night and 25 degrees Celsius maximum day.

2

The following observations, measurements and comparisons describe plants grown in Salinas, Calif., and in Bogota, Colombia under greenhouse conditions which approximate those generally used in commercial greenhouse practice. The low temperature tolerance was determined in repeated flowerings in Bogota, Colombia.

The following traits have been repeatedly observed and are determined to be basic characteristics of Ocaso, which, in combination, distinguish this Chrysanthemum as a new and distinct cultivar:

1. Flat capitulum form.
2. Daisy capitulum type.
3. Orange-bronze ray floret color.
4. Diameter across face of capitulum of 83 to 89 mm when fully opened.
5. Flowering response in Salinas under normal temperatures is 45 to 49 days after start of short days. Flowering response in Bogota, Colombia under minimum 7 degrees Celsius night and maximum 29 degrees Celsius day is 62 to 65 days after start of short days.
6. Peduncle length of the first lateral at flowering after removing the apical bud without growth regulator applications is 15 to 18 cm when grown in Salinas, Calif., and 18 to 20 cm when grown in Bogota, Colombia. Peduncle length of the fourth lateral at flowering is 20 to 23 cm when grown in Salinas, and 20 to 23 cm when grown in Bogota.
7. Plant height is 86 to 102 cm when grown in Salinas with 6 to 8 long days prior to start of short days, and 94–112 cm when grown in Bogota with 14 to 15 long days prior to start of short days.
8. Excellent tolerance to low night temperatures for bud initiation and flower development. Average minimum low night temperatures in our Bogota trials ranged from 7 to 8.5 degrees Celsius.

The above measurements represent repeated flowerings over a period of a minimum of two years.

The accompanying photographic drawings show typical inflorescence and leaf characteristics of Ocaso, with the colors being as nearly true as possible with illustrations of this type.

Sheet 1 is a color photograph of Ocaso grown as a single stem cut spray mum.

Sheet 2 is a black and white photograph of three views of the inflorescence of Ocaso.

Sheet 3 is a black and white photograph showing the upper and under sides of the leaves of Ocaso at three stages of development (mature, intermediate and immature).

Of the cultivars known to the inventor, the most similar in comparison to Ocaso is the cultivar identified as Paleto, a bronze daisy spray cut mum disclosed in U.S. Plant Pat. No. 6,903. Reference is made to attached Chart A, which compares certain characteristics of Ocaso to the same characteristics of Paleto.

Similar traits are capitulum form and type, spray formation, and low night temperature tolerance. The ray floret color of both Ocaso and Paleto is generally described as orange-bronze. However, the ray floret color of Ocaso is a lighter, brighter, more vibrant orange-bronze than the color of Paleto, described in the plant patent therefor as being closest to 163A to 163B, a more grayed-orange color. Ocaso also has a larger diameter of capitulum and a shorter flowering response than Paleto.

In the following description color references are made to The Royal Horticultural Society Colour Chart. The color values were determined on plant material grown in Salinas, Calif. on July 27, 1989.

Classification:

*Botanical.*—*Dendranthema grandiflora* cv Ocaso.

*Commercial.*—Daisy cut spray mum.

INFLORESCENCE

A. Capitulum:

*Form.*—Flat.

*Type.*—Daisy.

*Diameter across face.*—83 to 89 mm when fully opened.

B. Corolla of ray florets:

*Color (general tonality from a distance of three meters).*—Orange-bronze.

*Color (upper surface).*—Closest to 21B, tinged with 22A towards base; tinged with 14B towards apex.

*Color (under surface).*—14B, tinged with 9B.

*Shape.*—Straight, cross-section concave.

C. Corolla of disc florets:

*Color (mature).*—Closest to 14A.

*Color (immature).*—Closest to 144B to 144C. Under certain conditions the center of the disc shows a small brown dot, closest to 166B to 166C. This is visible in both the color and black and white photographs.

D. Reproductive organs:

*Androecium.*—Present on disc florets only; no pollen.

*Gynoecium.*—Present on both ray and disc florets.

PLANT

A. General appearance:

*Height.*—86 to 102 cm when grown as a single stem cut mum with 6 to 8 long days prior to start of short days in Salinas, Calif.; 94 to 112 cm when grown as a single stem cut mum with 14 to 15 long days prior to start of short days in Bogota, Colombia.

B. Foliage:

*Color (upper surface).*—147A.

*Color (under surface).*—147B.

*Shape.*—See photograph.

CHART A

COMPARISON OF OCASO AND PALETO

| CHARACTERISTIC | OCASO | PALETO |
|---|---|---|
| Ray floret color | Orange-bronze | Orange-bronze |
| Capitulum form | Flat | Flat |
| Capitulum type | Daisy | Daisy |
| Spray formation | Terminal | Terminal |
| Peduncle length | | |
| 1st lateral, Salinas | 15 to 18 cm | 10 to 15 cm |
| 4th lateral, Salinas | 20 to 23 cm | 18 to 23 cm |
| 1st lateral, Bogota | 18 to 20 cm | 15 to 23 cm |
| 4th lateral, Bogota | 20 to 23 cm | 20 to 25 cm |
| Diameter across face of capitulum | 83 to 89 mm | 70 to 89 mm |
| Plant height | | |
| 6–8 long days, Salinas | 86 to 102 cm | 81 to 86 cm |
| 14–15 long days, Bogota | 94 to 112 cm | 107 to 114 cm |
| Flowering response period | | |
| in Salinas | 45 to 49 days | 51 to 56 days |
| in Bogota | 62 to 65 days | 70 to 76 days |
| Low night temperature tolerance | Excellent | Excellent |

Comparisons Made of Plants Grown as Single Stem Spray Cut Mums in Salinas, California, and in Bogota, Colombia

I claim:

1. A new and distinct Chrysanthemum plant named Ocaso, as described and illustrated.

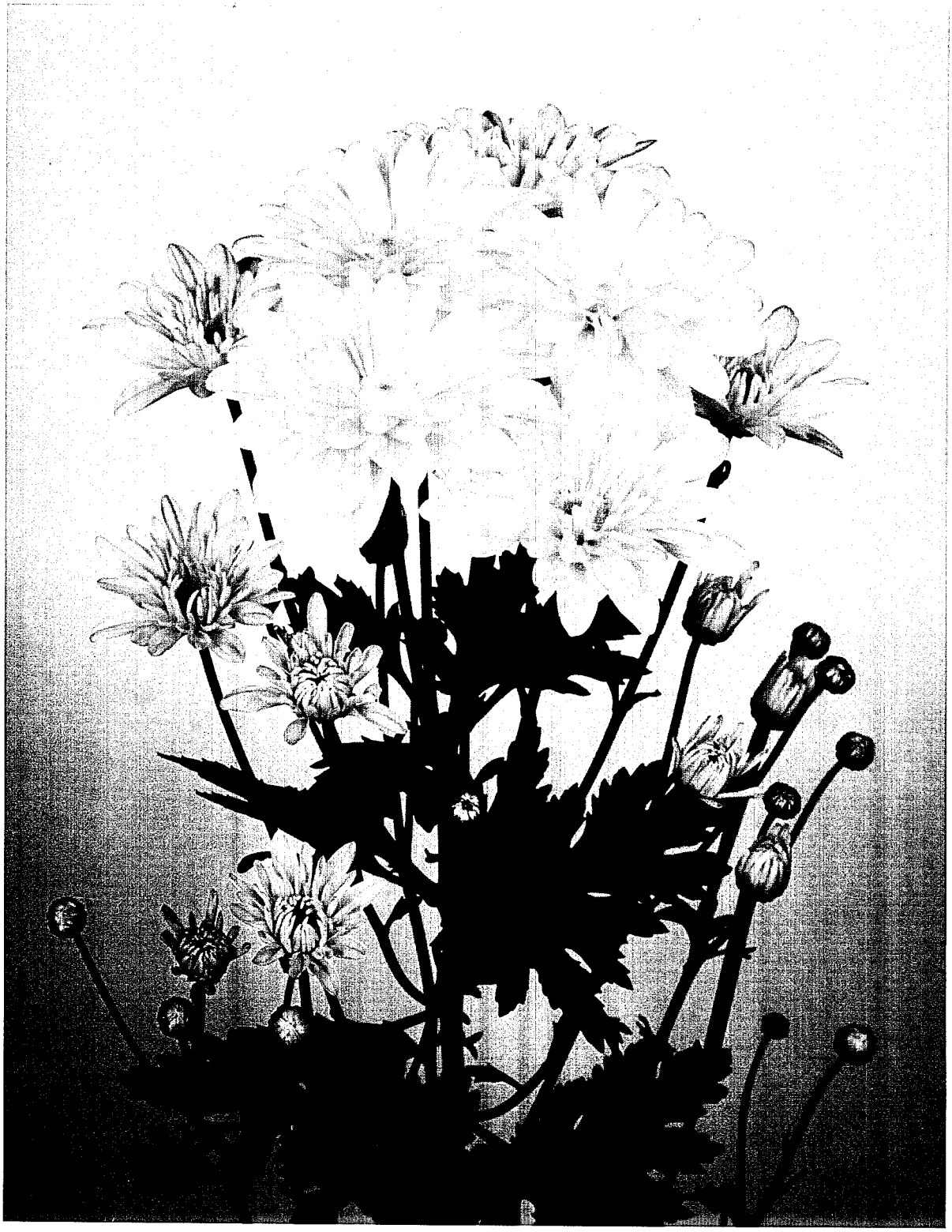

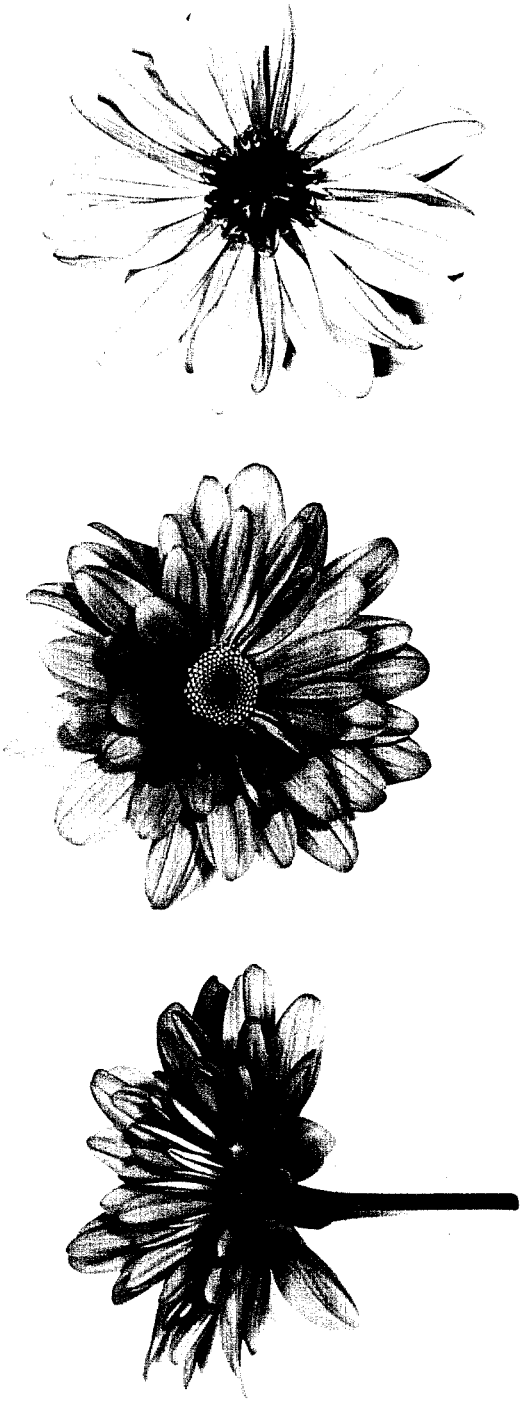

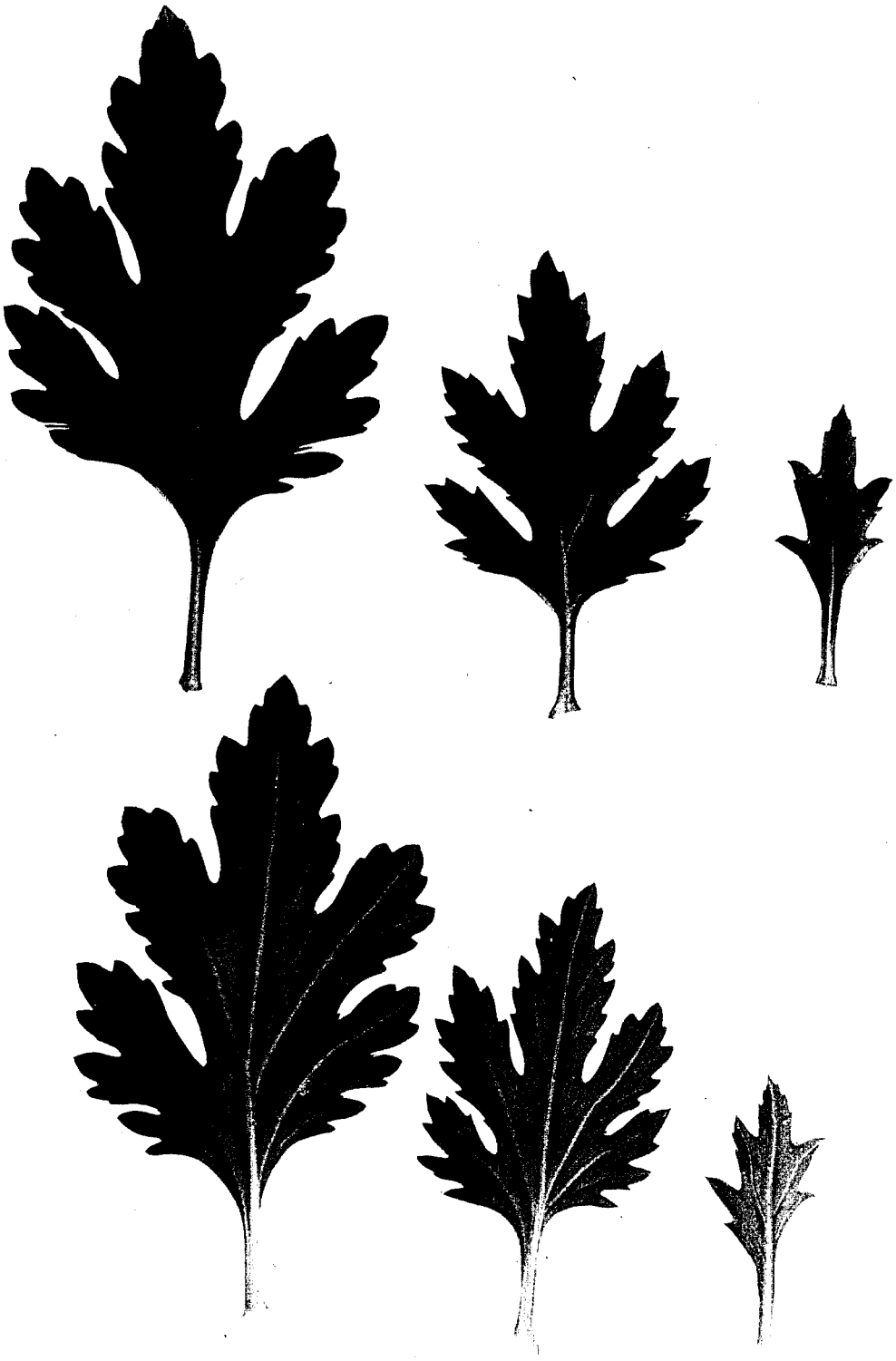

* * * * *